United States Patent [19]

Ilizarov

[11] Patent Number: 5,067,954
[45] Date of Patent: Nov. 26, 1991

[54] DISTRACTION APPARATUS FOR PLASTIC RECONSTRUCTION OF HAND

[76] Inventor: Gavriil A. Ilizarov, ulitsa Klimova, 41, kv. 38., Kurgan, U.S.S.R.

[21] Appl. No.: 490,629
[22] PCT Filed: Jul. 25, 1988
[86] PCT No.: PCT/SU88/00140
    § 371 Date: Mar. 20, 1990
    § 102(e) Date: Mar. 20, 1990
[87] PCT Pub. No.: WO90/00882
    PCT Pub. Date: Feb. 8, 1990

[51] Int. Cl.$^5$ ............................................. A61B 17/00
[52] U.S. Cl. ........................................ 606/58; 606/54; 606/57
[58] Field of Search .................. 606/53, 54, 55, 56, 606/57, 58, 59

[56] References Cited

U.S. PATENT DOCUMENTS

| | | | |
|---|---|---|---|
| 3,941,123 | 3/1976 | Volkov et al. | 606/55 |
| 3,985,127 | 10/1976 | Volkov et al. | 606/55 |
| 3,993,055 | 11/1976 | Volkov et al. | 606/55 |
| 4,338,927 | 7/1982 | Volkov et al. | 606/55 |
| 4,624,249 | 11/1986 | Cambras | 606/57 |
| 4,889,111 | 12/1989 | Ben-dov | 606/54 |
| 4,978,347 | 12/1980 | Ilazarov | 606/54 |

FOREIGN PATENT DOCUMENTS

| | | | |
|---|---|---|---|
| 0912156 | 3/1982 | U.S.S.R. | 606/56 |
| 959768 | 9/1982 | U.S.S.R. | 606/55 |
| 1237189 | 6/1986 | U.S.S.R. | |
| 1371695 | 2/1988 | U.S.S.R. | |
| 1398853 | 5/1988 | U.S.S.R. | |
| 2040168 | 8/1980 | United Kingdom | 606/56 |

OTHER PUBLICATIONS

Proceedings of the Second International Symposium on Improvements of Apparatus and Methods for External Fixation, vol. 1, 1985, Riga.
'Improvement in Treatment of Fractures-Dislocations of the anterior and Middle Foot Segments Using an External Fixation Apparatus' by V. V. Klyuchevsky et al., pp. 184-186 (in Russian).

Primary Examiner—Stephen C. Pellegrino
Assistant Examiner—Glenn K. Dawson
Attorney, Agent, or Firm—Lilling and Lilling

[57] ABSTRACT

In a distraction apparatus for plastic reconstruction of hand, having a proximal support made as a cramp-shaped plate carrying two fixing pins, a distal support carrying distraction pins, and two distraction threaded rods on which the proximal support and the distal support are fitted, according to the invention, the fixing pins are arranged in a plane square with the planes of the cramp-shaped plate, while the distal support is made as a bar having perforations, wherein additional distraction threaded rods are fitted, the distraction pins being held with their distal ends to the proximal ends of the additional distraction threaded rods.

4 Claims, 4 Drawing Sheets

DISTRACTION APPARATUS FOR PLASTIC RECONSTRUCTION OF HAND

BACKGROUND OF THE INVENTION

1. Field of the Invention

The invention relates to medical engineering applied in orthopedics and traumatology and has particular reference to distraction apparatus for plastic reconstruction of the hand.

2. Description of the Related Art

Congenital adactyly or digital hypoplasia, as well as morbid conditions secondary to an injury to digits, are one of the most urgent problems of surgery of the hand. This is concerned with the fact that the hand plays an immense part in human activities. Thus, lack of fingers or underdeveloped hand inflict not only moral but also physical distress upon a patient. Such a person proves to be most frequently not only disabled from any industrial work but cannot also perform self-servicing to provide his/her activities in everyday life.

Attempts made for formation of fingers and plastic reconstruction of the hand using transplants, intra-and extraosseous fixation means in clinical practice have proved to be ineffective, since it is impossible to provide a sufficient amount of soft tissues for simultaneous loading of the transplant and formation of digits. Fixation methods and means for their practical application are imperfect due to their being unreliable and causative of a traumatic lesion.

Apparatus for external fixation of injured bones prove to be a more efficacious means for solving the aforesaid problem.

A prior-art apparatus for distraction of dislocations in the metacarpophalangeal and metatarsophalangeal joints (SU, A, 912,156) is known to comprise traction stirrups carrying fixing pins, pin holders and distraction rods. The stirrups are interconnected to form a closed frame whose opposite sides carry the distraction rods arranged in a row and mounting the fixing pins provided with thrust flats.

The apparatus is capable of differentiated reduction of multiple inveterate disclocations of the metacarophalengeal and metatarsophalangeal joints. Reduction of the 2nd, 3rd, 4th and 5th metacarpophalangeal joints is carried out by alternate distraction with the aid of a pair of distraction rods that lock one pin guided through the respective bones. However, the given construction of the apparatus fails to provide simultaneous stretching out of the bones and plastic reconstruction of the hand. In addition, passing of the pins with thrust flats in the dorsipalmar direction is fraught with considerable traumatic lesion of the tendons and ligaments.

Known in the art presently is a distraction apparatus (SU, A, 1,237,189), comprising supports carrying pins fitted in pin clamps, distraction rods interconnecting the supports, one of which is shaped as an oval structure having holes, wherein U-shaped pins are held with the aid of pin clamps.

The aforesaid distraction apparatus provides access to the surface of the digital segment being stretched out. However, the pins secured on the side cylindrical surface of one of the supports fail to stretch out each of the digital segments separately; besides, soft tissues are liable to be cut through by the U-shaped pins in the course of stretching-out when securing the pins to the bone involved.

Another heretofore-known external fixation apparatus is essentially a more perfect one (cf. Proceedings of the Second International Symposium on Improvements of apparatus and methods for external fixation, vol. I, 1985, Riga, 'Improvement in treatment of fractures-dislocations of the anterior and middle foot segments using an external fixation apparatus' by V. V. Klyuchevsky et al., pp. 184-186 (in Russian). The apparatus comprises three semirings and two threaded rods. Two fixing pins are secured in the proximal semiring, while several distraction pins are held in the distal semiring by means of brackets. The semirings are interconnected through two threaded rods.

The aforesaid external fixation apparatus is used for treatment of fractures-dislocations in the Lisfranc's and Chopart's joints. However, the aforesaid apparatus features the fixing pins secured on the distal support with a possibility of performing once-through distraction by drawing up the pins manually. Besides, the pins are held to the distal support at an angle to the connecting threaded rods, which is necessary for treatment of fractures-dislocations of the plantar arch bones, whereas such an arrangement of the apparatus is not adapted for plastic reconstruction of the hand. Spin passage at an angle to the connecting threaded rods and to the longitudinal axis of the bone prevents the distal stump end from being invaginated into the soft-tissue digital rudiment.

SUMMARY OF THE INVENTION

It is therefore a primary and essential object of the present invention to provide a distraction apparatus for plastic reconstruction of the hand whose construction would make it possible to carry out separate stretching-out of each metacarpal bone or digital phalangeal stumps with simultaneous aligning of the distraction forces applied with the direction of the axis of the distraction pins, the connections of the regenerating portions of the bones to the apparatus being minimized.

The aforesaid object is accomplished in a distraction apparatus for plastic reconstruction of a hand, comprising at least two supports, viz., a proximal support made as a cramp-shaped plate carrying two parallel fixing pins each being secured at the ends of said plate, and a distal support carrying distraction pins secured therein with their distal ends with a possibility of longitudinal motion, as well as two distraction threaded rods, wherein the proximal and the distal supports are fitted with their ends so as to perform relative motion. According to the invention, the fixing pins of the proximal support are arranged in a plane square with the planes of the crampshaped plate, while the distal support is shaped as a perforated bar whose perforations are spread along its longitudinal axis parallel to the planes of the crampshaped plate, some additional distraction threaded rods being fitted in the perforations of the distal support bar with a possibility of relative motion, said additional distraction threaded rods being directed towards the proximal support, and the distal ends of the distraction pins are fastened on the proximal ends of the additional distraction threaded rods.

The fact that the fixing pins of the proximal support are arranged in a plane square with the planes of the cramp-shaped plate makes it possible to ensure against injury to the tendovaginal structures of the hand and places no limitations on the function of the joints in the course of treatment.

Provision of additional distraction threaded rods fitted in the perforations of the distal support bar which is parallel to the planes of the cramp-shaped plate, with a possibility of relative motion towards the proximal support, said rods carrying distraction pins held thereto, makes it possible to carry out separate stretching-out of each metacarpal bone or digital phalangeal stumps and thus to form a cosmetically perfect and correctly functioning hand.

It is possible that additional distraction rods be fitted in the perforations coaxially therewith and be axially traversable with respect to said holes.

Such a construction arrangement of the distraction apparatus for plastic reconstruction of hand makes it possible to carry out graduated distraction of each metacarpal bone separately lengthwise the bone axis.

According to an alternative embodiment of the invention, the additional distraction rods are expedient to be fitted in the perforations of the distal support bar by means of brackets with a possibility of performing relative angular and longitudinal travel, the longitudinal axes of the perforations being square with the longitudinal axes of the additional distraction rods.

Such a construction arrangement of the distraction apparatus provides for smooth directional motion of the additional distraction rods lengthwise their longitudinal axis with a possibility of their simultaneous travel towards the direction of divergent radii.

According to one more embodiment of the invention, the distraction apparatus for plastic reconstruction of the hand comprises an additional fixing pin, while the distraction rods are made up of two articulately interconnected portions, the ends of the additional fixing pin being secured on the respective distal portions of the distraction rods.

Such a construction arrangement of the distraction rods in combination with the additional fixing pin makes it possible to mobilize the joints adjacent to the bone segments being stretched out, thus making it possible to bring in time-coincidence the stretching-out of bones and plastic reconstruction of the hand and its functional rehabilitation.

BRIEF DESCRIPTION OF THE DRAWINGS

In what follows the distraction apparatus for plastic reconstruction of a hand is illustrated by specific exemplary embodiments thereof with reference to the accompanying drawings, wherein.

DESCRIPTION OF PREFERRED EMBODIMENT OF THE INVENTION

Figure 1:
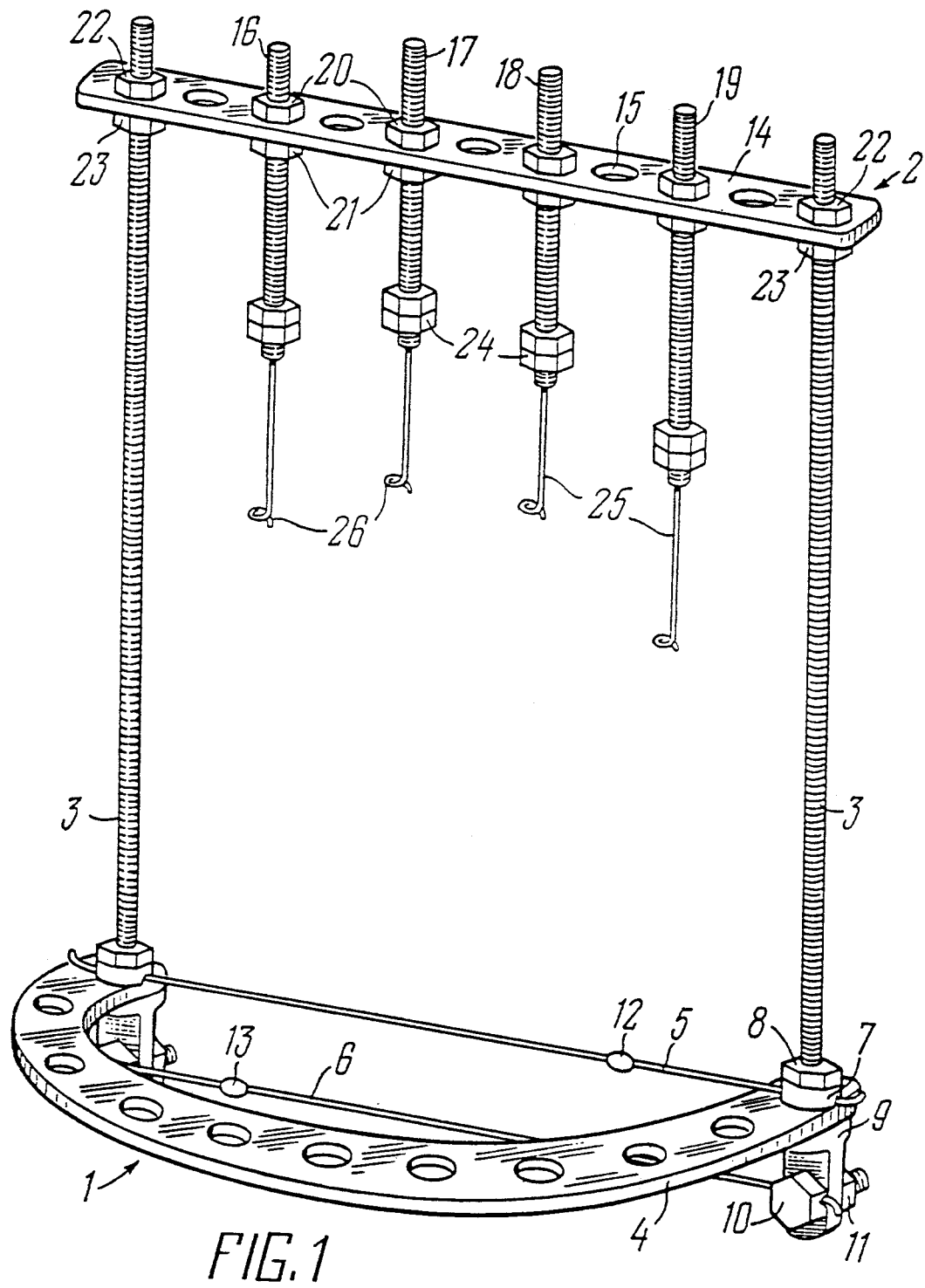
FIG. 1 is a general view of a distraction apparatus for plastic reconstruction of the hand, according to the invention.

Now, referring to the accompanying drawings, FIG. 1 shows the distraction apparatus for plastic reconstruction of a hand, according to the invention. The apparatus comprises a proximal support 1 and a distal support 2 interconnected by distraction threaded rods 3.

The proximal support 1 is made as a cramp-shaped plate 4 at whose ends are fitted parallel fixing pins 5 and 6. The fixing pin 5 is secured on the cramp-shaped plate 4 by means of a washer 7 and a nut 8 fitted on the distraction threaded rods 3 which pass through the perforations (omitted in the Drawings) provided at the ends of the cramp-shaped plates 4. The proximal ends of the distraction threaded rods 3 carry brackets 9 on which the fixing pin 6 is fastened with the aid of a bolt 10 and a nut 11. The brackets 9, the nuts 8 and the proximal ends of the distraction threaded rods 3 establish a rigid connection to the ends of the cramp-shaped plate 4. The pins 5 a nd 6 carry stops 12, 13 respectively.

The distal support 2 is made as a bar 14 having perforations 15, the plane of said bar being parallel to the plane of the cramp-shaped plate 4 and to the fixing pins 5, 6 of the proximal support 1. Additional distraction threaded rods 16, 17, 18, 19 are fitted, with their distal ends, in the perforations of the bar 14 with a possibility of performing axial travel by the aid of nuts 20, 21. The bar 14 is mounted at the distal ends of the distraction threaded rods 3 passing through the extreme perforations 15 with a possibility of moving along the distraction threaded rods 3 with the aid of nuts 22, 23.

The distal ends of distraction pins 25 provided with loop-shaped stops 26 are rigidly secured by means of nuts 24 at the proximal ends of the additional distraction threaded rods 16, 17, 18, 19.

Figure 2:
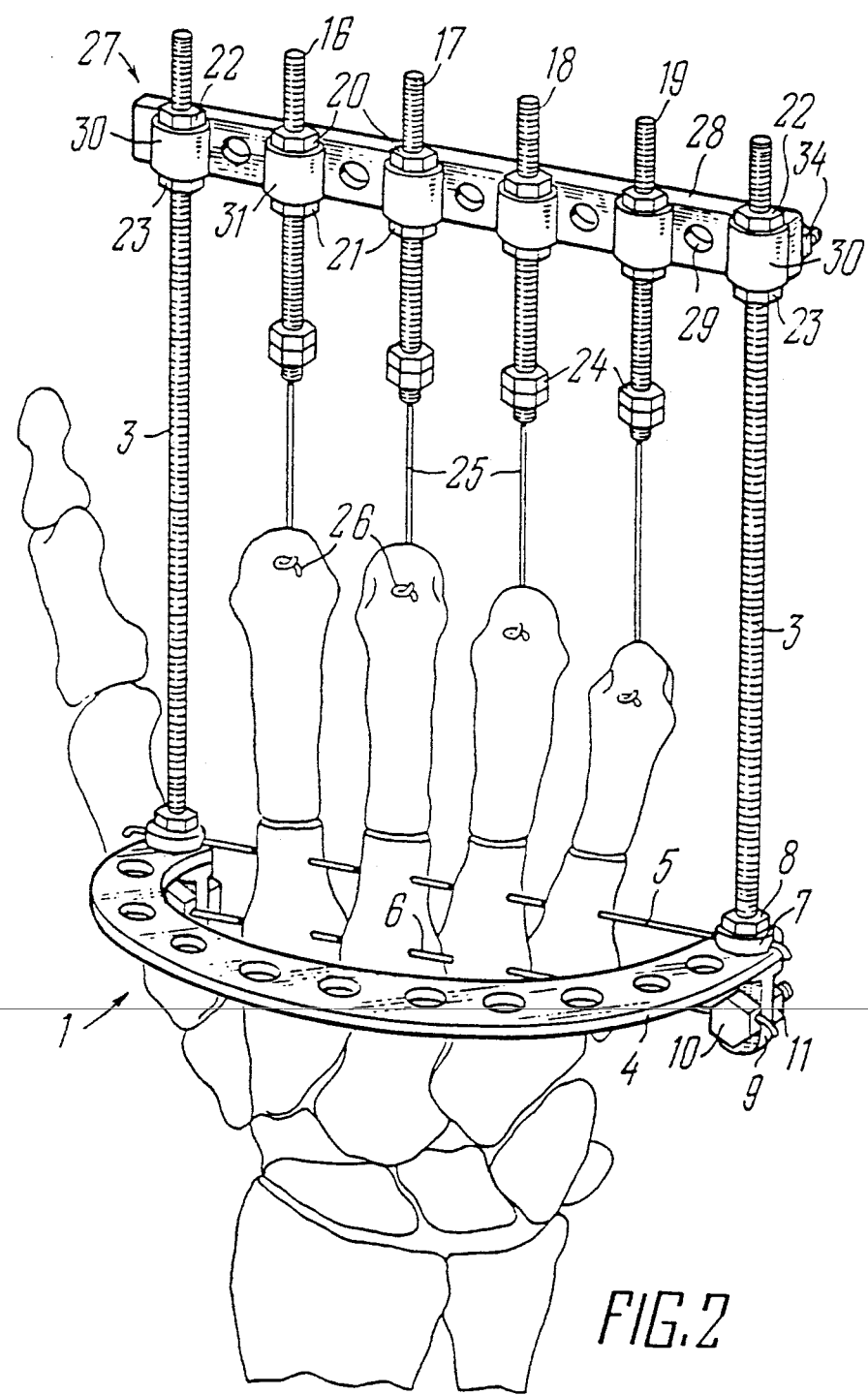
FIG. 2 is an embodiment of the distraction apparatus for plastic reconstruction of the hand, according to the invention, when placed on the metacarpal bones of the right hand.
Figure 3:
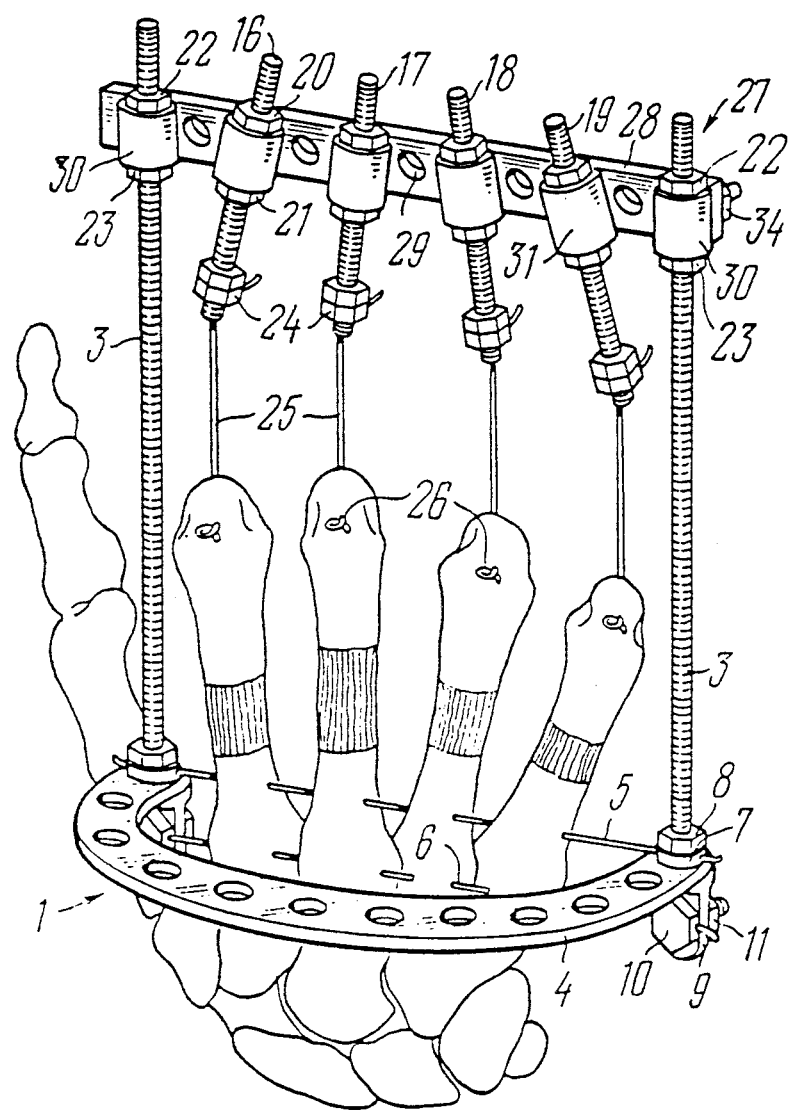
FIG. 3 is the embodiment of the distraction apparatus for plastic reconstruction of the hand of FIG. 2 shown in the process of stretching-out the metacarpal bones and plastic reconstruction of the hand.

An embodiment of the distraction apparatus for plastic reconstruction of the hand, according to the invention, illustrated in FIGS. 2, 3 comprises the proximal support 1 and a distal support 27 interconnected through the distraction threaded rods 3. The proximal support 1 is similar to that described in the preceding embodiment with the sole exception that the fixing pins 5, 6 fitted at the ends of the cramp-shaped plates 4 are devoid of stops.

The distal support 27 is made as a bar 28 having perforations 29, the plane of said support being square with the plane of the cramp-shaped plate 4 and parallel to the fixing pins 5, 6 of the proximal support 1.

Figure 4:
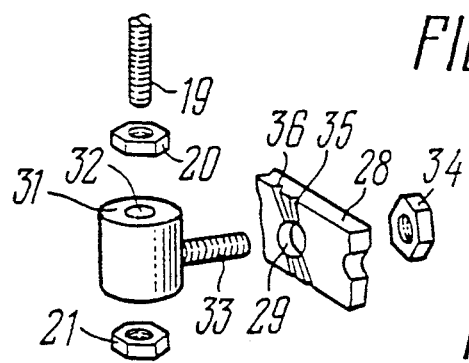
FIG. 4 is a view of an attachment unit of the bracket with bar (in disassembled state) in the embodiment of the distraction apparatus, according to the invention, as illustrated in FIG. 2.

The distal ends of the distraction threaded rods 3 and those of the additional distraction threaded rods 16, 17, 18, 19 carrying the distraction pins 25, are fitted in brackets 30, 31, respectively with a possibility of axial motion by means of the nuts 22, 23 and 20, 21, respectively. The brackets 30, 31 are similar to each other and appear as a cylinder with an axial hole 32 (FIG. 3) for fitting the distraction threaded rods 3 or the additional distraction threaded rods 16, 17, 18, 19, and a threaded rod 33 (FIG. 4) square with the axis of the hole 32 with the aid of which the brackets 30 and 31 are fitted in the perforations 29 of the bar 28 and locked with nuts 34.

Slots 35 are provided on the surface of the bar 28 on the side of location of the brackets 31 diametrally with respect to the respective perforations 29, said slots passing in parallel with the distraction threaded rods 3, and slots 36 running at an angle to the rods 3 for the brackets 31 to be set at an angle.

Figure 5:
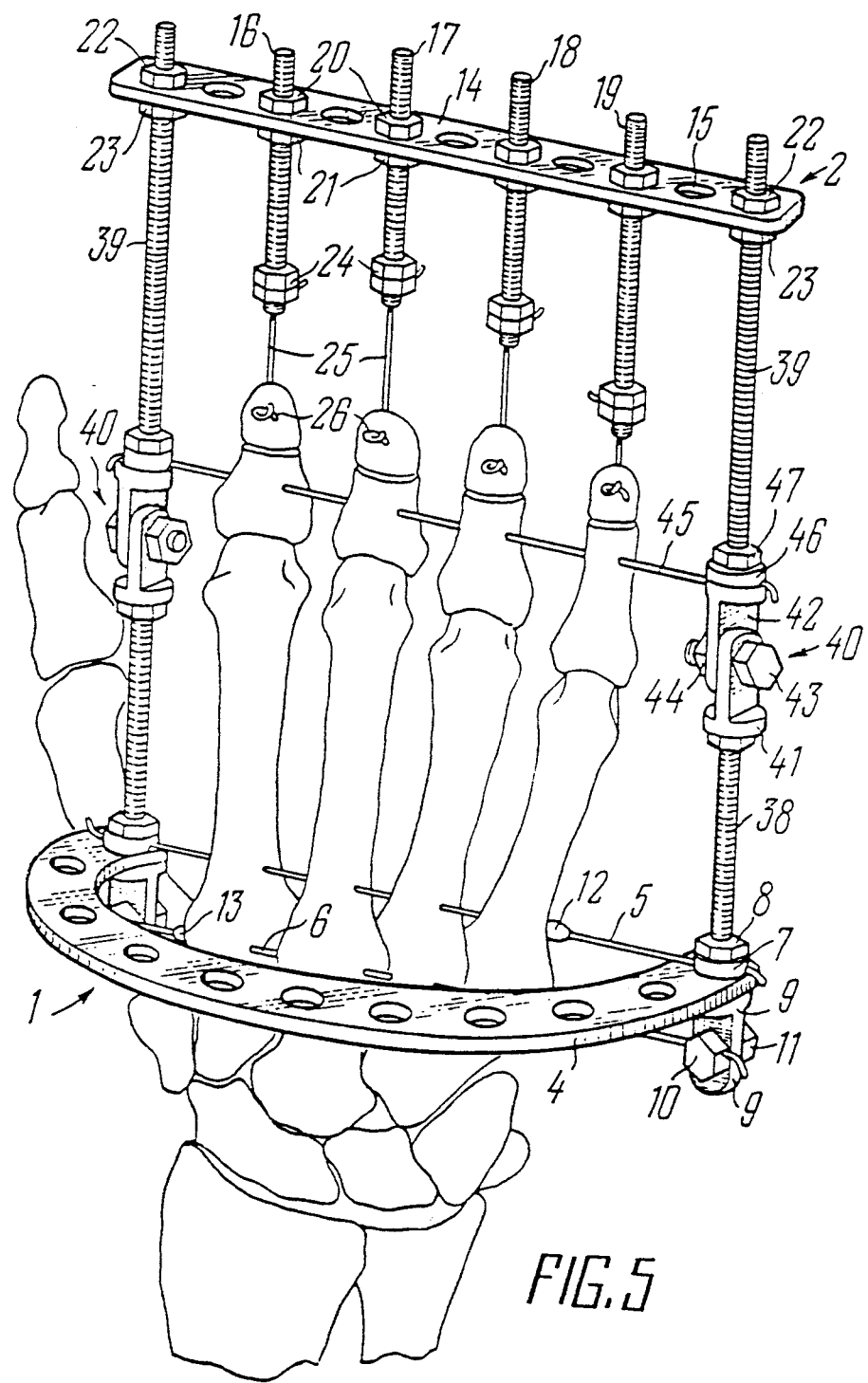
FIG. 5 is an embodiment of the distraction apparatus for plastic reconstruction of hand comprising an additional fixing pin and an articulately joined distraction threaded rods.

An alternative embodiment of the distraction apparatus, according to the invention, illustrated in FIG. 5 comprises the proximal support 1 and the distal support 2, both being similar to the embodiment shown in FIG. 1 and interconnected through distraction threaded rods 37, each of them being made up of two portions 38, 39 interconnected through articulated joints 40. The latter comprises two brackets 41, 42 made fast on the rods 38, 39, respectively and interconnected by a bolt 43 and a nut 44. The articulated joints 40 have common axis of rotation aligning with that of the metacarpophalangeal joints. The ends of an additional fixing pin 45 are secured on the brackets 42 with the aid of washers 46 and nuts 47, said pin being arranged parallel to the fixing pins 5, 6 of the proximal support 1.

The distraction apparatus for plastic reconstruction of a hand, according to the invention, is used as follows.

Two parallel pins 5 (FIG. 1), 6 having the respective stops 12, 13 are passed through the bases of the 2nd, 3rd, 4th, 5th metacarpal bones in a transverse direction of the hand from opposite sides thereof and are secured in the support 4 arranged in a plane square with that of the hand from its palmar side. The fixing pin 5 is fastened with the aid of the washer 7 and the nut 8, while the pin 6, by means of the bolt 10 and the nut 11. Then two small incisions are made in the palmar surface of the hand in the area of the second and fourth interdigital spaces, whereupon osteotomy of the 2nd, 3rd, 4th and 5th metacarpal bones is carried out with the aid of a chisel. Then the pin 25 having the stop 26 is passed through each of the distal portions of the 2nd, 3rd, 4th, 5th metacarpal bones in an oblique longitudinal direction so that the pointed end of the pin 25 is guided through the soft-tissue digital rudiment at the distal end of a congenital hand stump. The proximal end of the pin 25 is inserted under the skin till it rests against the bone, while the distal end of the pin 25 is bent towards the axis of the metacarpal bone and is connected, through the nuts 24, to the additional distraction rods 16, 17, 18, 19, whereupon the additional distraction rods 16, 17, 18, 19 are connected to the bar 14 by means of the perforations 15 and the nuts 20, 21.

Next the distal support 2 is fitted on the distraction rods 3 and secured in a required position by the nuts 22, 23. Once the primary osseous union has been formed, distraction of all bone fragments is carried out by moving the distal support, which is attained through drawing up the nuts 22, 23. Distraction of separate bone fragments is effected in the same way by drawing up the nuts 20, 21 with the purpose of moving any of the additional distraction rods 16, 17, 18, 19 until each of the fingers being formed reaches a required length.

Whenever it becomes necessary to increase the intermetacarpal spaces and stretch out the metacarpal bones, use is made of the distal support 27 (FIGS. 2, 3). Using rotatability of the bracket 31 about the bar 28, the additional distraction threaded rods 16, 17, 18, 19 are arranged either along the axes of the metacarpal bones or at an angle thereto by fitting the brackets 31 carrying the additional threaded rods 16, 17, 18, 19 in the respective slots 35, 36, which makes it possible to obtain the hand of a required shape. By drawing up the nuts 22, 23 on the distraction threaded rods 3 one can effect distraction of all the metacarpal bones at a time, though any of the metacarpal bones can be stretched out separately at an individual rate and pace due to drawing up the nuts 20, 21 on the additional distraction rods 16, 17, 18, 19 of the brackets 31. Use of the pin 25 having the stop 26 by passing it through the digital rudiment avoids skin cutting through during distraction and makes it possible to invaginate the distal fragment of the metacarpal bones into the soft-tissue rudimentary saccule of the respective finger with subsequent formation of the fingers. Whenever it is necessary to stretch out the principal phalanges of the 2nd, 3rd, 4th, 5th digits preserving mobility in the metacarpophalangeal joints use is made of the embodiment of the apparatus for plastic reconstruction of hand as shown in FIG. 5.

Two parallel pins 5, 6 having the stops 12, 13, respectively are passed through the bases of the 2nd, 3rd, 4th, 5th metacarpal bones from the opposite sides and are secured in the proximal support 1. Then the additional fixing pin 45 is passed through the basis of the 2nd, 3rd, 4th, 5th principal digital phalanges, and the ends of said pin is held to the proximal portion of the distraction rods 39 using the washer 46 and the nut 47.

The pin 25 having the stop 26 is passed through each of the distal portions of the 2nd, 3rd, 4th, 5th principal digital phalanges in an obliquelongitudinal direction, and the distal portion of said pins are connected to the additional threaded rods 16, 17, 18, 19 in the distal support 2. It is also possible to simultaneously stretch out all digits by moving the distal support 2 along the distraction rods 39 by means of the nuts 22, 23, or to separately stretch out each of the digits at an individual rate and pace by drawing up the nuts 20, 21 on the additional rods 16, 17, 18, 19 on the bar 14.

The present distraction apparatus for plastic reconstruction of the hand can find most utility when applied for stretching out shortened segments of the hand, digital stumps and metacarpal bones for plastic reconstruction of such hand without using transplants.

The proposed construction of a distraction apparatus for plastic reconstruction of the hand provides for optimum conditions for X-ray monitoring of the state of reparation osteogenesis of the fragments of the metacarpol bones, especially in the direct projection, when clearness of the image in the side projection is affected due to interference with the image of the adjacent bones.

The present distraction apparatus for plastic reconstruction of the hand enables one to retain the orticular interstices, thus making possible performance of both passive and active movements within the early postoperative period when simultaneously stretching out the abnormally short digital phalanges.

What is claimed is:

1. A distraction apparatus for plastic reconstruction of a hand, comprising: at least two supports, a proximal support of said supports being made as a cramp-shaped plate carrying two parallel fixing pins secured at ends of said plate, and a distal support of said supports carrying distraction pins secured within the distal support with a possibility of longitudinal motion, as well as two distraction threaded rods on which the proximal support and the distal support are fitted so as to perform relative longitudinal motion, the fixing pins of the proximal support being arranged in a plane perpendicular with a plane of the cramp-shaped plate, the distal support being shaped as a bar having perforations spread along a longitudinal axis of the bar, said longitudinal axis of the bar being parallel to the plane of the cramp-shaped plate, additional distraction threaded rods being fitted in the perforations of the bar of the distal support with a possibility of individual longitudinal motion, said additional distraction threaded rods being directed towards the proximal support, distal ends of the distraction pins being fastened on proximal ends of the additional distraction threaded rods.

2. An apparatus as claimed in claim 1, wherein the additional distraction threaded rods are fitted coaxially in the perforations of the bar of the distal support and are axially traversable therewith.

3. An apparatus as claimed in claim 1, wherein the additional distraction threaded rods are fitted in the perforations of the bar of the distal support by brackets allowing relative angular and longitudinal travel of the additional distraction threaded rods, longitudinal axes of the perforations of the bar being perpendicular with longitudinal axes of the additional distraction threaded rods.

4. An apparatus as claimed in any one of the preceding claims, further comprising an additional fixing pin, the distraction threaded rods comprising two articulately interconnected portions, ends of the additional fixing pin being secured on respective distal portions of the distraction threaded rods.

* * * * *